Figure 1:
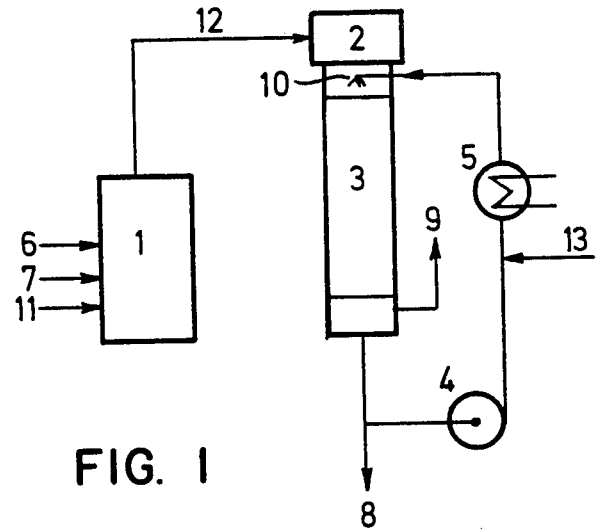

United States Patent [19]

Sauer et al.

[11] 4,440,960
[45] Apr. 3, 1984

[54] CONTINUOUS PREPARATION OF 3-ALKYL-BUTEN-1-ALS

[75] Inventors: Wolfgang Sauer, Kirchheimbolanden; Werner Aquila, Mannheim; Wolfgang Hoffmann, Frankenthal; Karl Brenner, Ludwigshafen; Klaus Halbritter, Mannheim, all of Fed. Rep. of Germany

[73] Assignee: BASF Aktiengesellschaft, Fed. Rep. of Germany

[21] Appl. No.: 330,024

[22] Filed: Dec. 11, 1981

[30] Foreign Application Priority Data

Dec. 31, 1980 [DE] Fed. Rep. of Germany ....... 3049543

[51] Int. Cl.³ ............................................. C07C 45/29
[52] U.S. Cl. ...................................... 568/471; 568/473
[58] Field of Search ................................. 568/471, 473

[56] References Cited

U.S. PATENT DOCUMENTS

| 2,042,320 | 5/1936 | Groll et al. | 568/471 |
| 2,682,560 | 6/1954 | Carter et al. | 568/471 |
| 3,944,623 | 3/1976 | Chabardes et al. | 568/471 |
| 3,948,997 | 4/1976 | Howe et al. | 568/473 |
| 4,097,535 | 6/1978 | Kaye et al. | 568/473 |
| 4,165,342 | 8/1979 | Dudeck et al. | 568/471 |

FOREIGN PATENT DOCUMENTS

| 2715209 | 10/1978 | Fed. Rep. of Germany | 568/471 |
| 2715208 | 10/1978 | Fed. Rep. of Germany | 568/471 |
| 2922599 | 12/1980 | Fed. Rep. of Germany | 568/471 |

Primary Examiner—Werren B. Lone
Attorney, Agent, or Firm—Keil & Witherspoon

[57] ABSTRACT

A process for the continuous preparation of 3-alkyl-buten-1-als by oxidative dehydrogenation of 3-alkyl-buten-1-ols at from 320° to 650° C. with oxygen over a catalyst containing copper and/or silver, wherein, within one second after contact with the catalyst, the vaporous reaction mixture, which is at from 320° to 650° C., is brought into contact with a liquid comprising water and/or the condensed reaction mixture at from −20° to 50° C., and the 3-alkyl-buten-1-als are separated off from the resulting condensate.

3 Claims, 4 Drawing Figures

CONTINUOUS PREPARATION OF 3-ALKYL-BUTEN-1-ALS

The present invention relates to a novel process for the continuous preparation of 3-alkyl-buten-1-als by oxidative dehydrogenation of 3-alkyl-buten-1-ols over copper and/or silver catalysts.

German Laid-Open Application DOS No. 2,715,209 discloses that 3-alkyl-buten-1-als can be prepared in a continuous process by oxidative dehydrogenation of the corresponding alcohols with oxygen over a silver and/or copper catalyst bed at from 320° to 650° C. The hot reaction gases are condensed and the 3-alkyl-buten-1-als are separated off. The preferred starting material 3-methyl-but-3-en-1-ol gives yields of 3-methyl-but-3-en-1-al of 76.6 and 81%, based on the 3-methyl-but-3-en-1-ol reacted, at conversions of 80.7 and 84.1% respectively.

This process is unsatisfactory regarding simple and economical operation, good yield and purity of the aldehydes and removal of the by-products. It is also a disadvantage that the condenser units frequently become blocked within a short time, so that continuous operation is impeded. The cracked products and polymers, some of which dissolve in the reaction products obtained, contaminate the product solutions to such an extent that problems such as increased formation of residues and losses of yield occur during further processing of the crude product. Moreover, great expense is necessary in purification of the crude product, in order to remove the by-products.

We have found that considerably more advantageous results are achieved in a process for the continuous preparation of 3-alkyl-buten-1-als of the formula

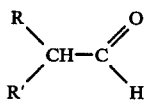

where R is hydrogen and R' is $H_2C=C(CH_3)-$, or R and R' together are $H_3C-C(CH_3)=$, by oxidative dehydrogenation of 3-alkyl-buten-1-ols of the formula

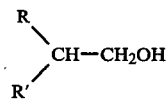

where R and R' have the above meanings, by passing these compounds and oxygen over a catalyst containing copper and/or silver at from 320° to 650° C., condensing the reaction gases and separating off the 3-alkyl-buten-1-als, wherein, within one second after contact with the catalyst, the vaporous reaction mixture, which is at from 320° to 650° C., is brought into contact with a liquid comprising water and/or the condensed reaction mixture at from −20° to 50° C., and the 3-alkyl-buten-1-als are separated off from the resulting condensate.

Compared with the conventional processes, the process according to the invention surprisingly gives a better overall result with respect to yield and purity of the end products, by a simpler and more economical route.

The oxidative dehydrogenation of the 3-alkyl-buten-1-ols with oxygen over the catalyst is initially carried out in a conventional manner, for example as disclosed in German Laid-Open Application DOS 2,715,209, at from 320° to 650° C., preferably from 400° to 600° C. In the process according to the invention, immediately after the resulting vaporous reaction mixture, which is at from 320° to 650° C., has left the catalyst bed, it is brought into contact with a liquid which causes instant condensation of the oxidation products. The condensing liquid used is water, the condensed liquid reaction mixture, or a mixture of these two liquids, preferably the aqueous or organic phase of the two-phase condensate obtained when the reaction mixtures are condensed. In a particularly advantageous embodiment of the invention, the aqueous phase is used as the condensing liquid. If condensed reaction mixtures are used as the condensing liquid, the excess condensate which is not recycled as cooled condensing liquid is removed as crude product and, where relevant, worked up or reacted further.

The vaporous reaction mixture which is obtained in the oxidation and, as described, is treated with the condensing liquid for condensation of the products has, for example, the following composition (percentages are by weight): 34.5% of 3-methyl-but-3-en-1-al, 6.7% of 3-methyl-but-2-en-1-al, 12.6% of 3-methyl-but-3-en-1-ol, 1.2% of high-boiling organic products, 0.3% of acids, 0.3% of formaldehyde, 2.1% of isobutene, 2.2% of carbon monoxide, 2.4% of carbon dioxide, 13.4% of water, 0.7% of hydrogen and 23.6% of nitrogen.

It is essential that the vaporous reaction mixture, which is at from 320° to 650° C., is brought into contact with the condensing liquid within one second. The condensing liquid is preferably at from −20° to 50° C. This treatment is carried out, for example, by passing the stream of hot reaction gases directly into a quenching chamber which is immediately downstream of the catalyst bed. Preferably, the condensing liquid is brought into contact with the reactor gases in the form of droplets having an average diameter of from 1 to 2,000 micrometers. The droplets are produced with the aid of conventional atomizing devices, in particular jets. The condensing liquid is advantageously sprayed into the quenching chamber so that most of the droplets meet the stream of reaction gases at an angle of from 2° to 85° to the axis of flow.

The amount of condensing liquid (also called quenching liquid in the Examples) is advantageously from 20 to 100 parts by weight per part by weight of the reaction gases. After condensation, the liquid condensate has, for example, the following composition (percentages are by weight): 50.1% of 3-methyl-but-3-en-1-al, 9.6% of 3-methyl-but-2-en-1-al, 18.3% of 3-methyl-but-3-en-1-ol, 1.7% of high-boiling organic products, 0.5% of acids, 0.5% of formaldehyde and 19.3% of water.

The condensates are worked up, in order to separate off the 3-alkyl-buten-1-als, in a conventional manner, for example by fractional distillation. In this operation, the 3-alkyl-buten-1-als prepared, being lower-boiling components, can be separated from the 3-alkyl-buten-1-ol starting material and isolated. If the 3-alkyl-but-2-en-1-al is to be prepared, the 3-alkyl-but-3-en-1-al obtained in the process according to the invention can be catalytically isomerized directly in the reaction mixture, in the manner described in German Laid-Open Applications DOS No. 2,715,208 and DOS No. 2,715,209, and the isomer can then be isolated by fractional distillation.

The yields in the case of the reaction of 3-methyl-but-3-en-1-ol are increased by about 10% by the process according to the invention. At the same time, the content of some of the atmosphere-polluting substances in the off-gas, such as carbon monoxide, hydrocarbons and formaldehyde, is significantly reduced, so that purification of the off-gases can be improved. Working up of the crude products is also simplified, because of the lower level of by-products, in particular of high-boilers and components which form high-boilers. In comparison with the process of German Laid-Open Application DOS No. 2,715,209, decomposition of the hot reaction gases and blockages of the tube connections and units in the condensing equipment are avoided or substantially reduced. Trouble-free operation of the units is thus considerably improved and the profitability is increased.

There are other advantages of the process according to the invention, in respect of direct further processing of the crude products without prior working up, since the purity, for example measured according to color number, acid number and residue content of the crude products obtained are better by comparison, so that the secondary products can also be prepared in a better yield and purity.

These advantageous results were not to be expected, since 3-alkyl-buten-1-als, being unsaturated aliphatic aldehydes, are known to be very reactive substances (c.f. Ullmann, 4th edition, volume 7, page 118 et seq., especially 130-133). For example, they are readily oxidized to the corresponding carboxylic acids, form Diels-Alder adducts, readily polymerize and undergo a large number of addition reactions. Many of these reactions are accelerated by a polar medium and traces of acids, bases or salts.

It is therefore surprising that when the hot reaction gases are brought into contact with the finely divided condensing liquid, by-product formation is not increased since, compared with the process in German Laid-Open Application DOS No. 2,715,209, a significantly greater contact area of non-condensing reactive components in the reaction gas, such as oxygen, hydrogen, carbon monoxide, formaldehyde and isobutene, is presented to the 3-alkyl-buten-1-al, and water and other concomitant substances which promote by-product formation, such as acids, are also present. An increase in the formation of by-products was to be expected particularly, in the preferred embodiment in which recycled aqueous product solution is used as the condensing liquid, since the very reactive unsaturated aldehyde is continually being exposed to the hot reaction gases whilst it is in the form of finely divided droplets, a form which greatly promotes reaction.

In the following Examples, parts are by weight.

EXAMPLE 1 (FIG. 1)

A unit with an alcohol vaporizer (1), appropriate feed lines for alcohol (6), water (7) and air or nitrogen (11) and a vertical tube reactor (2) is used. The feed line (12) for the vaporous starting mixture and the reactor cover are located at the head of the reactor. The catalyst bed is below the reactor head, and immediately below this is the quenching chamber (10), which forms the head of a packed column (3). At the bottom of the column is a line (8) for taking off the condensed liquid reaction product. So that some of the liquid reaction products can be used as quenching liquid, the line (8) is connected to a pump (4), by means of which the liquid can be sprayed, via a heat exchanger (5) and a jet system, into the quenching chamber. The off-gas escapes via line (9).

A catalyst consisting of silver crystals (28 parts) and having the following composition is introduced into the reactor (2):

|  | Proportion of catalyst percent by weight | Particle size mm |
|---|---|---|
| Layer 1 (top) | 21.4 | 0.2–0.4 |
| Layer 2 (middle) | 50.0 | 0.4–0.75 |
| Layer 3 (middle) | 23.6 | 0.75–1.0 |
| Layer 4 (bottom) | 5.0 | 1.0–2.5 |

The total depth of the catalyst bed before the start of the reaction is 20 mm.

The catalyst is heated externally to 460° C. 80 parts of 3-methyl-but-3-en-1-ol are introduced into the vaporizer (1) via line (6) and are heated to 125° C. 100 parts per hour of air are then passed into the vaporizer via line (11). The gaseous starting mixture flows through line (12) into the reactor (10), whereupon the temperature of the catalyst starts to rise. When the reaction starts, recognizable by the increase in catalyst temperature, the air flow is brought to 182 parts per hour and at the same time the amount of 3-methyl-but-3-en-1-ol passed through the catalyst is brought to 361 parts per hour in the course of 0.1 hour. This corresponds to a throughput over the catalyst of 1.15 t of 3-methyl-but-3-en-1-ol per hour per square meter of catalyst bed cross-section. In addition, 64 parts per hour of water in the form of steam are passed over the catalyst via line (7), vaporizer (1) and line (12). When the external heating is removed, a reaction temperature of 485° C. is established in the silver and a pressure of 1.10 bar is established upstream of the catalyst. The residence time of the gases in the catalyst chamber is 0.008 second.

The reaction gases issuing from the catalyst bed at 485° C. are brought into contact with the quenching liquid in the form of droplets in the quenching chamber (10). The droplets are produced by 2 rings, each with 6 staggered jets, which are located symmetrically on the wall of the column (3). The jets are charged, via the pump (4) and the heat exchanger (5), with the heterogeneous mixture of the aqueous and organic product phase from the reaction, which is branched off line (8) and circulated as quenching liquid. The angle at which the droplets meet the axis of flow varies for each jet and is from 15° to 75°. For 70% of the droplets, this angle is from 30° to 75°. The droplets have an average diameter of 200 micrometers.

The residence time of the reaction gases between the catalyst bed and the quenching chamber is 0.05 second, and the residence time in the quenching chamber is 1 second. The gas is at 470° C. before entry into the quenching chamber, the quenching liquid is at 1° C., the gases are at 16° C. after leaving the quenching chamber, and the amount of quenching liquid is 30,000 parts per hour.

The amount of heterogeneous mixture of aqueous and organic phase obtained per unit time from the reaction is removed continuously via line (8).

203 parts of 3-methyl-but-3-en-1-al and 39 parts of 3-methyl-but-2-en-1-al, as well as 74 parts of unreacted 3-methyl-but-3-en-1-ol, are obtained per hour. The conversion is 79.5%, and the total yield of 3-methylbutenal is 86.3% of theory, based on 3-methyl-buten-1-ol converted.

7 parts per hour of high-boiling condensation and polymerization products are obtained as undesirable impurities in the product solution removed. 12 parts of isobutylene, 13 parts of carbon monoxide and 14 parts of carbon dioxide are removed as other essential by-products in the off-gas of the reaction via line (9).

The synthesis was carried out without problems, in the manner described, for 60 days, no blockages as a result of deposits in the quenching chamber or in the downstream packed column occurring. The yield and product quality remained unchanged.

EXAMPLE 2 (FIG. 2)

Figure 2:
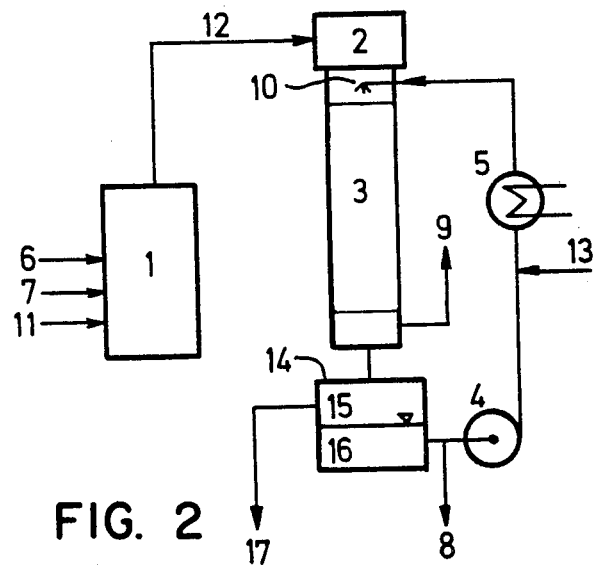

A mixture of 361 parts of 3-methyl-but-3-en-1-ol, 64 parts of water and 182 parts of air per hour is passed over loose catalyst at 485° C. and under a pressure of 1.10 bar by a procedure similar to that in Example 1 in a unit such as that shown in FIG. 2, which comprises the unit according to FIG. 1 and an additional phase separator (14). The residence time of the gases in the catalyst chamber is 0.008 second. In the quenching chamber (10), the reaction gases issuing from the catalyst chamber (2) are brought into contact with droplets of an atomized quenching liquid consisting of the aqueous phase (16) of the reaction product, which has been separated into the aqueous and organic phases in the phase separation vessel (14). The quenching liquid is recycled via the pump (4) and the heat exchanger (5). The amount of aqueous phase obtained per unit time is continuously removed from the circulation via line (8). The organic phase (15) obtained is removed via line (17).

The droplets produced in the quenching chamber have an average diameter of 200 micrometers. The angle at which they meet the axis of flow is from 15° to 75°. For 70% of the droplets, this angle is from 30° to 75°.

The residence time of the reaction gases between the catalyst and quenching chamber is 0.05 second, and the residence time in the quenching chamber is 1 second.

The gases are at 470° C. before entry into the quenching chamber, the quenching liquid is at 1° C., the gases are at 11° C. after leaving the quenching chamber, and the amount of quenching liquid is 30,000 parts per hour.

199 parts of 3-methyl-but-3-en-1-al, 45 parts of 3-methyl-but-2-en-1-al and 74 parts of unreacted 3-methyl-but-3-en-1-ol per hour are removed via lines (8) and (17). The conversion is 79.5%, and the total yield of 3-methylbutenal is 87.0%, based on 3-methyl-but-3-en-1-ol converted.

7 parts per hour of high-boiling condensation and polymerization products are obtained as undesirable impurities in the product solution removed. 11 parts of isobutylene, 12 parts of carbon monoxide and 14 parts of carbon dioxide are removed as other essential by-products in the off-gas of the reaction via line (9).

The synthesis was operated without problems, in this manner, for 60 days, no blockages as a result of deposits in the quenching chamber or in the subsequent packed column occurring. The yield and product quality remained unchanged.

EXAMPLE 3 (FIG. 3)

Figure 3:
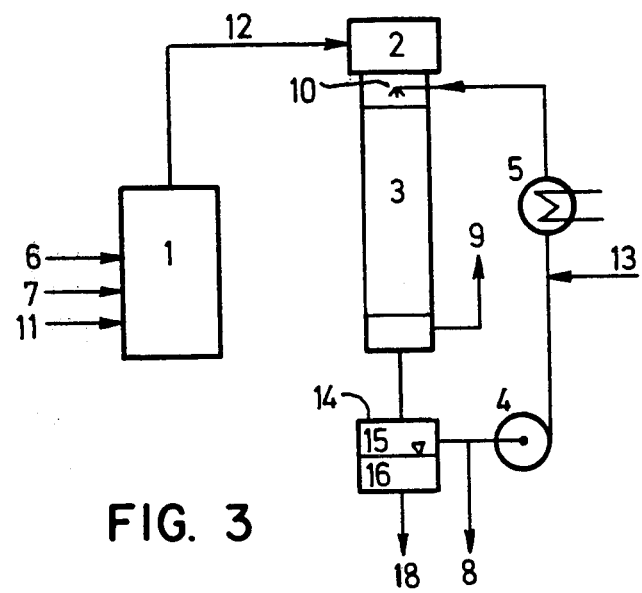

A mixture of 361 parts of 3-methyl-but-3-en-1-ol, 64 parts of water and 182 parts of air per hour is passed over the loose catalyst at 45° C. and under a pressure of 1.10 bar by a procedure similar to that in Example 1 in a variant of the unit shown in FIG. 3. The residence time of the gases in the catalyst chamber is 0.008 second.

In the quenching chamber (10), the reaction gases issuing from the catalyst chamber (2) are brought into contact with droplets of atomized quenching liquid, which consists of the organic phase (15) of the reaction product which has been separated into aqueous and organic phases in the phase separation vessel (14). The quenching liquid is recycled via the pump (4) and the heat exchanger (5). The amount of organic phase obtained per unit time is continuously removed from the circulation via line (8). The aqueous phase obtained is removed via line (18).

The droplets produced in the quenching chamber have an average diameter of 200 micrometers. The angle at which they meet the axis of flow is from 15° to 75°. For 70% of the droplets, this angle is from 30° to 75°.

The residence time of the reaction gases between the catalyst and the quenching chamber is 0.05 second, and the residence time in the quenching chamber is 1 second. The gases are at 470° C. before entry into the quenching chamber, the quenching liquid is at −10° C., the gases are at 9° C. after leaving the quenching chamber, and the amount of quenching liquid is 30,000 parts per hour.

205 parts of 3-methyl-but-3-en-1-al, 37 parts of 3-methyl-but-2-en-1-al and 74 parts of unreacted 3-methyl-but-3-en-1-ol per hour are removed via lines (8) and (18). The conversion is 79.5%, and the total yield of 3-methylbutenal is 86.3%, based on 3-methyl-but-3-en-1-ol converted.

8 parts per hour of high-boiling condensation and polymerization products are obtained as undesirable impurities in the product solution removed. 12 parts of isobutylene, 12 parts of carbon monoxide and 14 parts of carbon dioxide are removed as other essential by-products in the off-gas of the reaction via line (9).

The synthesis was operated without problems, in this manner for 60 days, no blockages as a result of deposits in the quenching chamber or in the subsequent packed column occurring. The yield and product quality remained unchanged.

COMPARATIVE EXAMPLE (FIG. 4)

Figure 4:
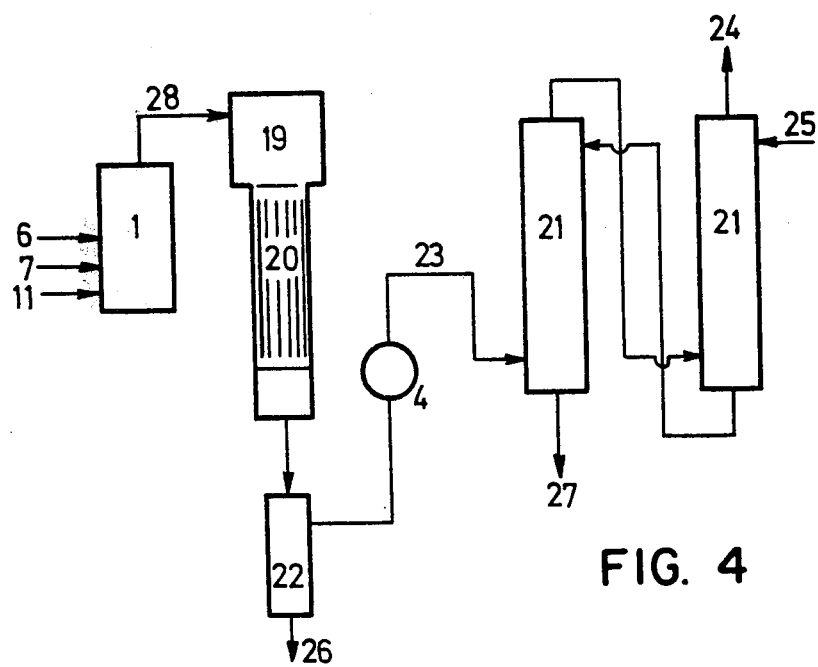

A unit consisting of a vaporizer (1), a vertical tube reactor (19), a downstream condenser (20) and an absorber (21), as shown in FIG. 4, is used. The vaporizer is connected to the tube reactor by line (28). The line can be heated as far as the reactor. The catalyst bed is below the reactor head, and below the bed is the condensing zone (20). The condensate formed in the condensing zone collects in the receiver (22), and the condensing zone is connected to the absorber (21) via a pump (4) and the line (23) (sic-in the Figure, the receiver is connected to the absorber via the pump and line). The absorber comprises two double-walled absorption columns which are arranged in a cascade and have outer-jacket cooling. The two columns are packed with 10 mm glass Raschig rings. The off-gas escapes via line (24).

A catalyst is introduced into the reactor (19), as described in Example 1. 361 parts of 3-methyl-but-3-en-1-ol, 64 parts of water and 182 parts of air per hour are passed through lines (6), (7) and (11) and over the catalyst bed at 485° C. and under a pressure of 1.08 bar by a procedure similar to that in Example 1. The residence time of the gases in the catalyst chamber is 0.008 second.

The reaction mixture is then cooled to 25° C. in the condensing zone of the reactor (20), some of it condensing and being collected in a receiver (22). Absorption in (21) is effected in two stages in the form of gas-washing in countercurrent. 840 parts per hour of dimethylformamide are introduced as the absorption liquid via line (25), the cascade (21) being at −10° C. The reaction mixture obtained in the condensation section and in the absorption section via lines (26) and (27) is distilled, the 3-methyl-but-3-en-1-al present being isomerized quantitatively to 3-methyl-but-2-en-1-al because of the catalytic action of the dimethylformamide used as the absorption liquid.

218 parts of 3-methyl-but-2-en-1-al and 70 parts of unreacted 3-methyl-but-3-en-1-ol per hour are obtained. The conversion is 80.6%, and the total yield of 3-methylbutenal is 76.6%, based on 3-methyl-but-3-en-1-ol converted.

13 parts per hour of high-boiling condensation and polymerization products are obtained as undesirable impurities in the product solution removed. 23 parts of isobutylene, 23 parts of carbon monoxide and 14 parts of carbon dioxide are removed as other essentially by-products in the off-gas of the reaction via line (24).

Over an operating period of 14 days, the pressure loss of the system rose from the initial value of 1.08 bar to 1.95 bar. The reason for this was the ever increasing blockage of the condenser (20) by deposited cracked products. Parallel to this, the content of high-boilers in the condensed product rose from 13 parts to 19 parts per hour, whilst discoloration of the condensate by dissolved cracked products simultaneously increased significantly. Over the same period, the amount of 3-methylbutenal obtained fell from 218 parts to 211 parts per hour, corresponding to a drop in yield from 76.7% to 74.2%, based on 3-methyl-but-3-en-1-ol reacted.

We claim:

1. A process for the continuous preparation of 3-alkyl-buten-1-als of the formula

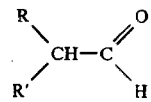

where R is hydrogen and R' is H₂C═C(CH₃)—, or R and R' together are H₃C—C(CH₃)═, by oxidative dehydrogenation of 3-alkyl-buten-1-ols of the formula

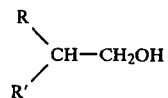                    I where R and R' have the above meanings, by passing these compounds and oxygen over a catalyst containing copper and/or silver at from 320° to 650° C., condensing the reaction gases and separating off the 3-alkyl-buten-1-als, wherein, within one second after contact with the catalyst, the vaporous reaction mixture, which is at from 320° to 650° C., is brought into contact with a liquid comprising water and/or the condensed reaction mixture at from −20° to 50° C., and the 3-alkyl-buten-1-als are separated off from the resulting condensate.

2. The process of claim 1, wherein the liquid consisting of water and/or the condensed reaction mixture is brought into contact with the reaction gases in the form of droplets having an average diameter of from 1 to 2,000 micrometers.

3. The process of claim 2, wherein most of the droplets meet the stream of reaction gases at an angle of from 2° to 85° to the axis of flow.

* * * * *